(12) United States Patent
Govari et al.

(10) Patent No.: US 7,367,970 B2
(45) Date of Patent: May 6, 2008

(54) EXTERNALLY APPLIED RF FOR PULMONARY VEIN ISOLATION

(75) Inventors: Assaf Govari, Haifa (IL); Yitzhack Schwartz, Haifa (IL)

(73) Assignee: Biosense Webster Inc., Diamond Bar, CA (US)

( * ) Notice: Subject to any disclaimer, the term of this patent is extended or adjusted under 35 U.S.C. 154(b) by 0 days.

(21) Appl. No.: 10/706,299

(22) Filed: Nov. 11, 2003

(65) Prior Publication Data

US 2005/0101946 A1    May 12, 2005

(51) Int. Cl.
*A61B 18/18* (2006.01)

(52) U.S. Cl. .......................................... 606/32

(58) Field of Classification Search .................... 606/1, 606/27–52
See application file for complete search history.

(56) References Cited

U.S. PATENT DOCUMENTS

| | | |
|---|---|---|
| 4,979,948 A | 12/1990 | Geddes et al. |
| 5,366,490 A | 11/1994 | Edwards et al. |
| 5,391,199 A | 2/1995 | Ben-Haim |
| 5,433,708 A | 7/1995 | Nichols et al. |
| 5,443,489 A | 8/1995 | Ben-Haim et al |
| 5,480,422 A | 1/1996 | Ben-Haim |
| 5,807,395 A | 9/1998 | Mulier et al. |
| 5,840,025 A | 11/1998 | Ben-Haim |
| 5,891,134 A | 4/1999 | Goble et al. |
| 5,938,660 A | 8/1999 | Swartz et al. |
| 5,954,665 A | 9/1999 | Ben-Haim |
| 5,971,983 A | 10/1999 | Lesh |
| 6,004,269 A | 12/1999 | Crowley et al. |
| 6,012,457 A | 1/2000 | Lesh |
| 6,024,740 A | 2/2000 | Lesh et al. |
| 6,064,902 A | 5/2000 | Haissaguerre et al. |
| 6,090,084 A | 7/2000 | Hassett et al. |

(Continued)

FOREIGN PATENT DOCUMENTS

| | | |
|---|---|---|
| WO | WO 96/05768 | 2/1996 |
| WO | WO 02/30331 | 4/2002 |
| WO | WO 02/30331 A | 4/2002 |
| WO | WO 0230331 A | 4/2002 |

OTHER PUBLICATIONS

David Keane, et al, "Linear Atrial Ablation with a Diode Laser and Fiberoptic Catheter", Circulation 100:e59-e60, 1999.

(Continued)

*Primary Examiner*—Roy D. Gibson
*Assistant Examiner*—Pete Vrettakos
(74) *Attorney, Agent, or Firm*—Ladas & Parry LLP (57) ABSTRACT

A resonant circuit is incorporated in a stent, which implantable in a pulmonary vein using known cardiac catheterization techniques. When an external RF field is generated at the resonant frequency of the stent, RF energy is re-radiated by the stent toward electroconductive tissue in the wall of the pulmonary vein, and produces a circumferential conduction block. The stent can be made of biodegradable materials, so that it eventually is resorbed. Following an ablation procedure, the stent may be left in situ. Repeated ablation can be performed using the inserted stent until it has been determined that the desired lesions have been formed. Furthermore, the same stent can potentially be used even years after being inserted should the treated arrhythmia reoccur or a new arrhythmia develop, thereby possibly obviating the need for an invasive procedure at that future time.

13 Claims, 4 Drawing Sheets

U.S. PATENT DOCUMENTS

| | | | |
|---|---|---|---|
| 6,117,101 | A | 9/2000 | Diederich et al. |
| 6,164,283 | A | 12/2000 | Lesh |
| 6,190,353 | B1 | 2/2001 | Makower et al. |
| 6,190,382 | B1 | 2/2001 | Ormsby et al. |
| 6,206,835 | B1 * | 3/2001 | Spillman et al. ............ 600/485 |
| 6,235,025 | B1 | 5/2001 | Swartz et al. |
| 6,245,064 | B1 | 6/2001 | Lesh et al. |
| 6,251,109 | B1 | 6/2001 | Hassett et al. |
| 6,280,385 | B1 * | 8/2001 | Melzer et al. .............. 600/423 |
| 6,305,378 | B1 | 10/2001 | Lesh |
| 6,484,118 | B1 | 11/2002 | Govari |
| 6,802,857 | B1 * | 10/2004 | Walsh et al. ............... 623/1.15 |
| 2003/0050557 | A1 | 3/2003 | Susil et al. |
| 2003/0216729 | A1 | 11/2003 | Marchitto et al. |

OTHER PUBLICATIONS

C. Pappone, et al, "Circumferential Radiofrequency Ablation of Pulmonary Vein Ostia", Circulation 102:2619-2628, 2000.

Melvin M. Scheinman, et al, "Nonpharmacological Approaches to Atrial Fibrillation", Circulation 103:2120-2125, 2001.

David L. Ware, et al, "Slow Intramural Heating with Diffused Laser Light A Unique Method for Deep Myocardial Coagulation", Circulation 99:1630-1636, 1999.

Mathias Fink, "Time-Reversed Acoustics", Scientific American, pp. 91-97, Nov. 1999.

John C. Middleton, et al, "Synthetic biodegradable Polymers as Medical Devices", Medical Plastics and Biomaterials Magazine, Mar. 1998.

S. Adam, et al, "Extracardiac Ablation of the Canine Atrioventricular Junction by Use of High-Intensity Focused Ultrasound", Circulation 100:203-208, 1999.

Andrea Natale, et al, "First Human Experience With Pulmonary Vein Isolation Using A Through-The-Balloon Circumferential Ultrasound Ablation System For Recurrent Atrial Fibrillation", Circulation 102:1879-1882, 2000.

* cited by examiner

EXTERNALLY APPLIED RF FOR PULMONARY VEIN ISOLATION

BACKGROUND OF THE INVENTION

1. Field of the Invention

This invention relates to methods and apparatus for the medical treatment of disease of the heart. More particularly, this invention relates to a method and apparatus for treating cardiac arrhythmias by ablating in a vicinity of pulmonary venous tissue using radiofrequency energy.

2. Description of the Related Art

Invasive cardiac ablation techniques are well-known in the art. For example, U.S. Pat. Nos. 5,443,489, 5,480,422 and 5,954,665 to Ben-Haim describe systems for ablating cardiac tissue. U.S. Pat. No. 5,807,395 to Mulier et al., and U.S. Pat. No. 6,190,382 to Ormsby et al., describe systems for ablating body tissue using radio frequency. U.S. Pat. Nos. 6,251,109 and 6,090,084 to Hassett et al., U.S. Pat. No. 6,117,101 to Diederich et al., U.S. Pat. Nos. 5,938,660 and 6,235,025 to Swartz et al., U.S. Pat. No. 6,245,064 to Lesh et al., U.S. Pat. Nos. 6,164,283, 6,305,378 and 5,971,983 to Lesh, U.S. Pat. No. 6,004,269 to Crowley et al., and U.S. Pat. No. 6,064,902 to Haissaguerre et al., describe apparatus for tissue ablation to treat atrial arrhythmia, primarily by ablating tissue located within the pulmonary veins or on the ostia of the pulmonary veins. U.S. Pat. No. 5,366,490 to Edwards et al. describes a method for applying destructive energy to a target tissue using a catheter.

More recently, circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

Radiofrequency ablation using multiple contiguous circumferential points, guided by electro-anatomical mapping is proposed in the document, *Circumferential Radiofrequency Ablation of Pulmonary Vein Ostia: A New Anatomic Approach for Curing Atrial Fibrillation*, Pappone C, et al., Circulation 102:2619-2628 (2000).

It has also been proposed to produce circumferential ablative lesions using ultrasound delivered through a balloon. This technique is described, for example, in the document, *First Human Experience With Pulmonary Vein Isolation Using a Through-the-Balloon Circumferential Ultrasound Ablation System for Recurrent Atrial Fibrillation*, Natale A, et al., Circulation 102:1879-1882 (2000).

PCT Publication WO 02/30331 to Walsh et al. describes a stent device that is geometrically adapted to irradiate an area that is confined primarily to the vascular endothelium, in order to ablate hyperplastic tissue growing around the stent. Radiation by the stent occurs when it is subjected to a RF field produced by an external scanner. Repeated ablation by this device is said to prevent blockage of the stent.

SUMMARY OF THE INVENTION

Improved apparatus and methods for electrically isolating the pulmonary vein by accomplishing a circumferential conduction block surrounding the pulmonary vein ostium are provided in accordance with a disclosed embodiment of the invention. Particularly, the invention provides an indwelling apparatus for repeating a therapeutic ablation of conductive tissue surrounding the pulmonary vein ostium. The indwelling apparatus can be biodegradable.

In embodiments of the invention, a resonant circuit is incorporated in a stent, which is adapted to be implanted in a pulmonary vein proximate the ostium of the left atrium. Implantation is accomplished by known cardiac catheterization techniques. When an external RF field is generated at the resonant frequency of the stent, RF energy is re-radiated by the stent toward electroconductive tissue in the wall of the pulmonary vein. This produces a circumferential conduction block, thereby electrically isolating the pulmonary vein from the left atrium. The stent may be left in situ. In some embodiments, the stent is made of biodegradable materials, so that it eventually is resorbed.

Advantageously, after the invasive portion of the procedure has been completed, repeated ablation can be performed using the inserted stent until it has been determined that the desired lesions have been formed. Furthermore, the same stent can potentially be used even years after being inserted, should the treated arrhythmia reoccur, or a new arrhythmia develop, thereby possibly obviating the need for an invasive procedure at that future time.

The invention provides a method for electrically isolating a cardiac chamber, which is carried out by introducing a resonant circuit into an operative position proximate an ostium of a pulmonary vein, and generating an electromagnetic field at a site remote from the resonant circuit, wherein the resonant circuit is operatively included in the electromagnetic field. The electromagnetic field has a frequency substantially equal to the resonant frequency of the resonant circuit, causing the resonant circuit to re-radiate electromagnetic energy so as to ablate intramural target tissue in the pulmonary vein.

In an aspect of the method the electromagnetic field is generated until a conduction block at the target tissue is confirmed.

In another aspect of the method the resonant circuit is included in a stent, the resonant circuit is introduced by circumferentially engaging the stent with an inner wall of the pulmonary vein to define a circumferential region of contact between the stent and the pulmonary vein, wherein a principal axis of the stent is substantially aligned coaxially with the pulmonary vein.

One aspect of the method includes automatically calibrating the stent to resonate at a frequency of the electromagnetic field.

In one aspect of the method, circumferentially engaging the stent is accomplished by radially expanding the stent.

According to an additional aspect of the method, the stent is constructed of an alloy that has a shape memory.

Still another aspect of the method includes varying the temperature of the stent to alter its configuration.

In yet another aspect of the method, while varying the temperature, the stent radially expands responsive to its shape memory.

According to a further aspect of the method, the stent is constructed of a biodegradable material.

In one aspect of the method, after generating an electromagnetic field, the stent is left at the operative position, and thereafter the step of generating an electromagnetic field is repeated.

The invention provides a system for electrically isolating a cardiac chamber, including a resonant circuit adapted for introduction into an operative position in a pulmonary vein proximate an ostium thereof. The resonant circuit re-radiates radiofrequency energy responsively to an externally generated electromagnetic field that has a frequency substantially equal to the resonant frequency of the resonant circuit, the electromagnetic field causing the resonant circuit to re-radiate the radiofrequency energy so as to ablate intramural target tissue in the pulmonary vein.

The system may include a sensor for monitoring electrophysiologic cardiac properties of a subject for determining if a predefined end point has been reached. The predefined end point can be confirmation of a conduction block at the target tissue.

A further aspect of the system includes a stent dimensioned for circumferentially engagement with an inner wall of the pulmonary vein to define a circumferential region of contact between the stent and the pulmonary vein, wherein a principal axis of the stent is substantially aligned coaxially with the pulmonary vein. The resonant circuit is incorporated in the stent.

Another aspect of the system includes a plurality of capacitors in the resonant circuit, and a control circuit for automatically selecting one of the capacitors responsively to a frequency of the electromagnetic field so as to conform the resonant frequency of the resonant circuit with the frequency of the electromagnetic field.

According to another aspect of the system, the stent is constructed of an alloy has a shape memory.

According to one aspect of the system, the stent is constructed of a biodegradable material.

The invention provides a system for electrically isolating a cardiac chamber, including a resonant circuit adapted for introduction into an operative position in a pulmonary vein of a subject proximate an ostium of the pulmonary vein, a catheter adapted to carry the resonant circuit into the operative position in the pulmonary vein, and a stent dimensioned for circumferential engagement with an inner wall of the pulmonary vein to define a circumferential region of contact between the stent and the pulmonary vein. A principal axis of the stent is substantially aligned coaxially with the pulmonary vein, and the resonant circuit is incorporated in the stent. The system includes a generator disposed external to the subject for generating an electromagnetic field that has a frequency substantially equal to the resonant frequency of the resonant circuit, the electromagnetic field operatively including the resonant circuit and causing the resonant circuit to re-radiate electromagnetic energy so as to ablate intramural target tissue in the pulmonary vein.

An additional aspect of the system includes a sensor for monitoring electrophysiologic cardiac properties of the subject for determining if a predefined end point has been reached.

According to still another aspect of the system, the predefined end point is confirmation of a conduction block at the target tissue.

A further aspect of the system includes a plurality of capacitors in the resonant circuit, and a control circuit for automatically selecting one of the capacitors responsively to a frequency of the electromagnetic field so as to conform the resonant frequency of the resonant circuit with the frequency of the electromagnetic field.

An additional aspect of the system includes a localizing subsystem for tracking a position and orientation of the catheter, including a plurality of localizing field generators disposed external to the subject, a position sensor on the catheter that is responsive to localizing electromagnetic fields produced by the localizing field generators, and a receiver responsive to an output of the position sensor.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits and control logic have not been shown in detail in order not to unnecessarily obscure the present invention.

System Architecture

Figure 1:
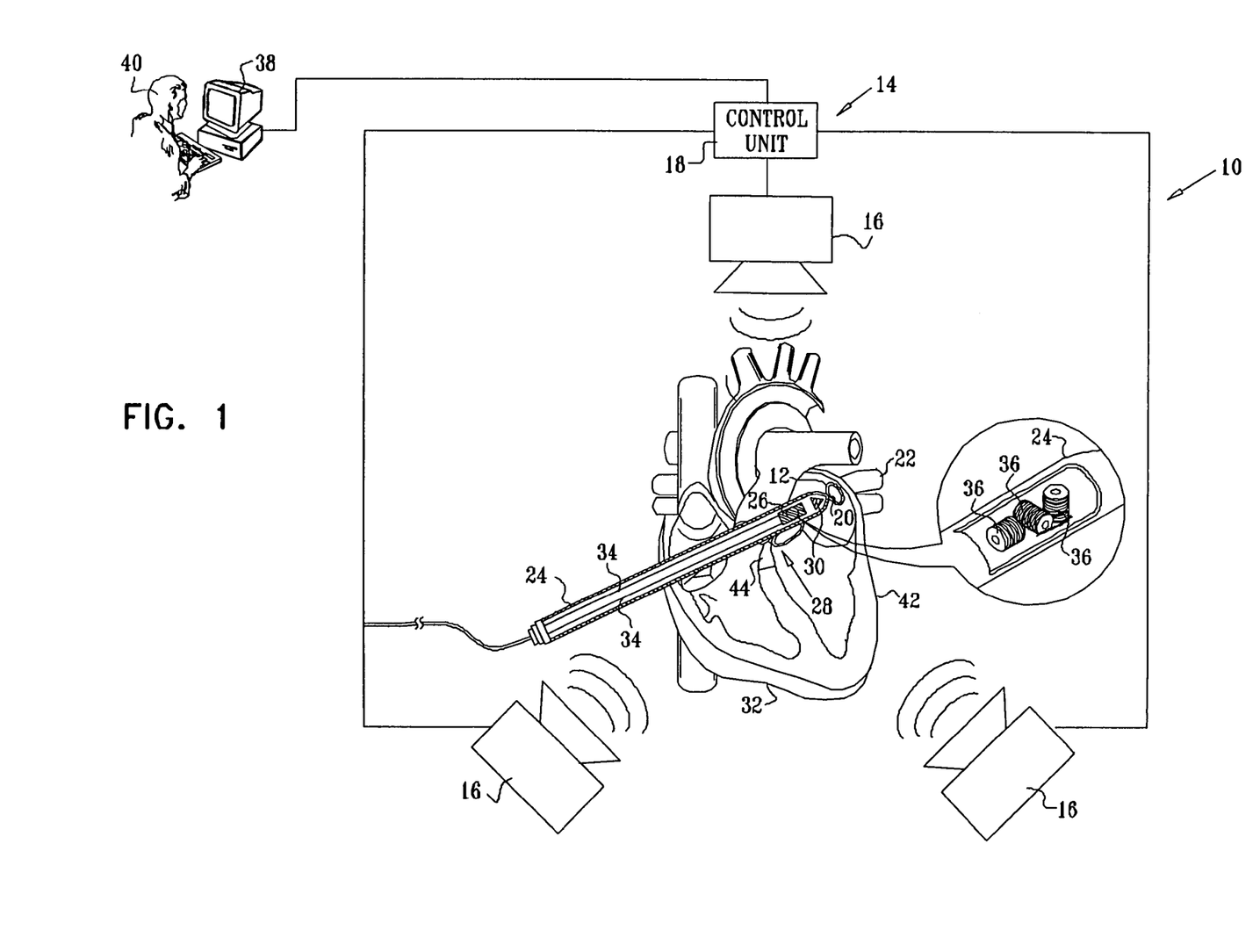
FIG. 1 is a schematic illustration of an ablation system that is constructed and operative in accordance with a disclosed embodiment of the invention.

Turning now to the drawings, reference is initially made to FIG. 1, which is a schematic illustration of an ablation system 10 that is constructed and operative in accordance with a disclosed embodiment of the invention. The system 10 is adapted to ablate target tissue 12 of a patient, and has a locating and mapping subsystem 14 that includes a plurality of radiofrequency (RF) transmitters 16 coupled to a control unit 18. The transmitters 16 can operate in a low-power mode for purposes of location and mapping, and in a high-power mode for purposes of target tissue ablation. Alternatively, separate transmitters may be provided for location sensing and for ablation. A stent 20 having a resonant circuit is disposed in a pulmonary vein 22 proximate the target tissue 12 to be ablated, as shown in further detail hereinbelow. In some embodiments, the stent 20 is dimensioned so as to engage the pulmonary vein. An outer diameter of 3 cm is suitable.

In other embodiments, in which it not intended to stent the pulmonary vein, but only to ablate target tissue, it is not required to physically engage the wall of the pulmonary vein at all in order to accomplish ablation. In such embodiments, it is only necessary that the resonant structure be positioned so as to include the target tissue within its operational range, after which it can be energized as further disclosed herein. Such embodiments have the advantage that in a single model, a relatively small resonant structure can be used for all applications, in patients of different ages and sizes, without need for accurately dimensioning the structure to the pulmonary vein or undertaking the construction required for the resonant structure to function as a stent.

To assist in inserting the stent at a desired site, a cardiac catheter 24 is used. The catheter 24 is provided with a sensor 26 for determination of the location of the catheter's distal segment 28, which carries the stent 20 during insertion. In some embodiments, the catheter 24 also has at least one monitoring electrode 30 for sensing electrical properties of the cardiac site. The target tissue 12 to be ablated can be located using the location and mapping system disclosed in commonly assigned U.S. Pat. Nos. 5,840,025 and 5,391,199, which are herein incorporated by reference. For the embodiment of U.S. Pat. No. 5,840,025, the monitoring electrode 30 may also serve as mapping electrodes. The electrodes detect local electrical activity of a heart 32, as a function of the location coordinates provided by the sensor 26. The distal segment 28 of the catheter 24 can be radio-opaque, in order to facilitate its localization by conventional radio-graphic techniques, alternatively or in addition to the system disclosed in the above-noted U.S. Pat. No. 5,840,025.

In an embodiment of the present invention, the sensor 26 is an electromagnetic position and orientation sensor, which receives electromagnetic field signals from a plurality of electromagnetic field transmitters 16, which are placed externally to the patient, on or near the body surface. During use, the transmitters 16 transmit electromagnetic fields to define a frame of reference in order to track the position and orientation of the distal segment 28 of the catheter 24. Thus, based on sensed electromagnetic fields, the sensor 26 transmits a location signal to the control unit 18 by providing at least 5 dimensions of position and orientation information (X, Y, Z, pitch and yaw) in the form of coordinate information. In some embodiments, six dimensions of position and orientation information (X, Y, Z, pitch, yaw and roll) are provided. The signal is transmitted by leads 34 in the catheter 24, which connect to the control unit 18. Alternatively, transmission of the signal from the sensor 26 to the control unit 18 may be wireless, in which case the control unit 18 is provided with a wireless receiver (not shown).

Understanding of the instant invention will be facilitated by a brief description of the locating and mapping subsystem 14 used to track the position of the distal segment 28, which is disclosed in the above-noted U.S. Pat. Nos. 5,840,025 and 5,391,199. The sensor 26 is used to sense the instantaneous position of the distal segment 28, and is typically an alternating current (AC) magnetic field receiver that senses magnetic fields generated by the transmitters 16. These transmitters generate AC magnetic fields to define a fixed frame of reference. Suitable sensors for use as the sensor 26 are further described in the above-noted U.S. Pat. No. 5,391,199 and further in PCT patent document WO96/05768 (U.S. patent application Ser. No. 08/793,371 filed May 14, 1997), the disclosure of which is incorporated herein by reference. The position and orientation coordinates of the distal segment 28 are then ascertained by determining the position and orientation coordinates of the sensor 26. The sensor 26 may comprise one or more antennas, for example one or more coils 36. It should be understood that placement of the transmitters 16, as well as their size and shape, will vary according to the application of the invention. Transmitters useful in a medical application comprise wound annular coils varying from about 2 to 20 cm in outer diameter, and from about 0.5 to 2 cm thick, in a coplanar, triangular arrangement, in which the centers of the coils are spaced apart by about 2 to 30 cm. Bar-shaped transmitters, triangular and square coils could all be useful for such medical applications. Moreover, in instances where a prone patient is the subject of a procedure involving the instant invention, the transmitters 16 are positioned at or below the surface upon which the patient is resting, substantially directly below the portion of the patient's body wherein a procedure is being performed. In other applications, the transmitters may be fairly close to the skin of the patient.

The transmitters 16 are driven by the control unit 18. The signals received by the sensor 26 are amplified and processed, together with a representation of the driving signals in a signal processor within the control unit 18 to provide an indication of the position and orientation of the distal segment 28. The transmitters 16 may be arranged in any convenient position and orientation, so long as they are fixed in respect to some reference frame, and so long as no two of the transmitters share the same location, i.e., position and orientation. When driven by the control unit 18, the transmitters 16 generate a multiplicity of distinguishable AC magnetic fields that are sensed by the sensor 26. The magnetic fields are distinguishable with regard to the frequency, phase, or both frequency and phase of the signals in the respective magnetic fields. Time multiplexing of the different magnetic fields is also possible.

The sensor 26 may consist of a single coil, but more commonly it has two or more and even three sensor coils 36 wound on either air cores or a core of material. The coils 36 have mutually orthogonal axes, one of which is conveniently aligned with the longitudinal axis of the catheter 24. The coils 36 are either interconnected, as shown in the inset of FIG. 1, or can be closely spaced along the longitudinal axis of the catheter 24 to reduce the diameter of the sensor 26. For most aspects of the present invention, quantitative measurement of the position and orientation of the distal segment 28 relative to a reference frame is necessary. This fixed frame of reference requires at least two non-overlapping transmitters 16 that generate at least two distinguishable AC magnetic fields for reception by the sensor 26. There should be at least two non-parallel coils 36 in the sensor 26 to measure the magnetic field flux resulting from the distinguishable magnetic fields. To determine six position and orientation coordinates (X, Y, Z directions and pitch, yaw and roll orientations) of the distal segment 28, it is desirable that at least two coils 36 and three transmitters 16 be present in the locating and mapping subsystem 14. Three coils would typically be used to improve the accuracy and reliability of the position measurement. In other applications, where fewer position and orientation coordinates are required, only a single coil may be necessary in the sensor 26. Specific features and functions of a single axis positioning system having only one coil are described in commonly assigned U.S. Pat. No. 6,484,118, which is incorporated herein by reference. In one embodiment the coils 36 have an inner diameter of 0.5 mm and have 800 turns of 16 micrometer diameter to give an overall coil diameter of 1-1.2 mm. The effective capture area of each coil is typically about 400 mm$^2$. It will be understood that these dimensions may vary over a considerable range. In particular, the size of the coils 36 can be as small as 0.3 mm (with some loss of sensitivity) and can exceed 2 mm. The wire size of the coils 36 can range from 10-31 micrometers, and the number of turns may vary between 300 and 2600, depending on the maximum allowable size and the wire diameter. The effective capture area should be made as large as feasible, consistent with the overall size requirements. While the usual sensor coil shape is cylindrical, other shapes can also be used. For example, a barrel-shaped coil can have more turns than a cylindrical coil of the same diameter.

The leads 34 carry signals detected by the sensor 26 to the control unit 18 for processing in order to generate the required position and orientation information. The leads 34 can be twisted pairs to reduce pick-up and may be further electrically shielded.

The sensor 26 is useful not only to determine when the distal segment 28 is in its operative position, but also to determine when the heart 32 is not in motion, for example during diastole. Alternatively, the sensor 26 can be omitted from the catheter 24, and the location of the distal segment 28 determined using other sensing or imaging means known to the art. In such case, other components of the locating and mapping subsystem 14 that are unneeded by such imaging means are also omitted.

A console 38 enables a physician 40 or other user to observe and regulate the functions of the catheter 24. The console 38 includes a computer, keyboard, and display. The console 38 also includes control circuits to permit control and operation of the catheter 24 and the control unit 18, and in particular to start and stop the collection of data.

A signal processor in the control unit 18 has circuits that receive, amplify, filter and digitize various signals received from the catheter 24, including signals generated by the sensor 26 and by the monitoring electrode 30. Circuits of the signal processor further compute the position and orientation of the distal segment 28 as well as the electrical characteristics of the portions of the heart 32 from the signals generated by the sensor 26 and the monitoring electrode 30. The circuits of the signal processor can also process body surface electrocardiogram signals. The digitized signals generated by the circuits of the signal processor are received by the computer of the console 38 for the reconstruction and visualization of an electrical or electromechanical map of a portion of the heart 32, for example a chamber wall 42 or interatrial septum 44.

Figure 2:
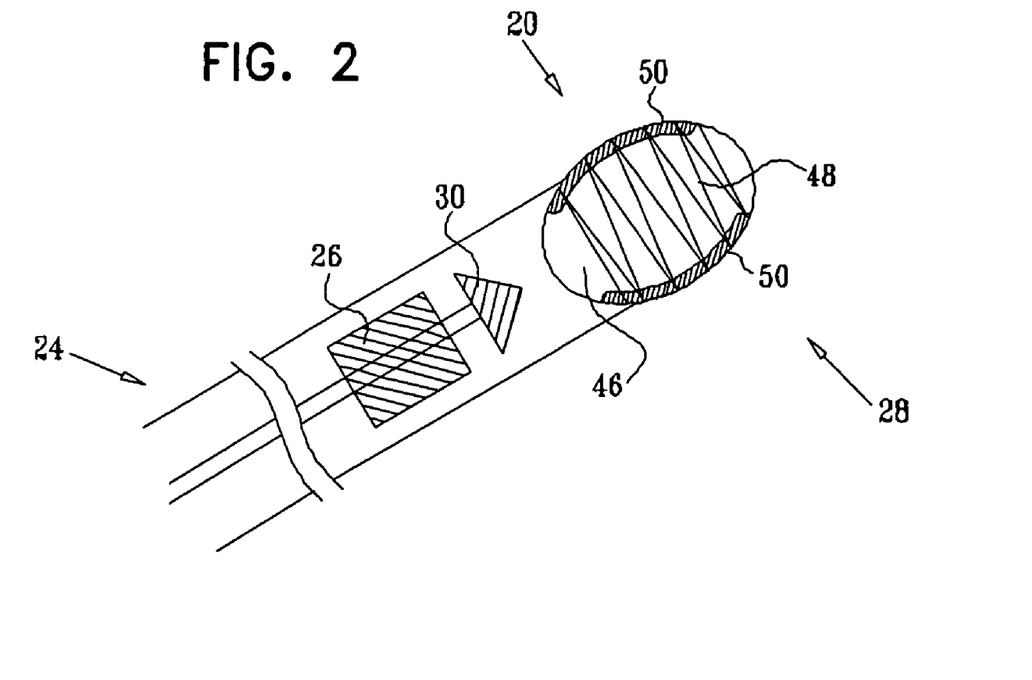
FIG. 2 is an enlarged schematic view of a distal segment of a catheter used in the ablation system shown in FIG. 1.

Reference is now made to FIG. 2, which is an enlarged schematic view of the distal segment 28 of the catheter 24 (FIG. 1). To perform an ablation procedure, the stent 20 is typically carried by an inflatable balloon 46 to a cardiac site of the patient proximate the target tissue 12 by the catheter 24. Structurally the stent 20 includes a coil 48, which is incorporated in or attached to a ring structure 50. The coil has a characteristic resonant frequency, which is used in the ablation process, as described hereinbelow. The ring structure 50 provides structural support for the coil 48, and may have dielectric properties. The balloon 46 is shown in an inflated state. However, during the insertion procedure it is typically at least partially deflated. The stent 20 can be fixed in place at its operative site by inflating the balloon 46, so as to urge the stent 20 against the inner wall of the pulmonary vein 22 (FIG. 1). Additionally or alternatively, resistive heating of the coil 48 may be employed to control expansion of the stent 20 within the pulmonary vein 22. Then, in order to withdraw the catheter 24, the balloon 46 is again deflated, at which time it separates from the stent 20, and the stent 20 remains attached to the pulmonary vein 22.

Alternatively, the stent 20 may comprise an elastic material, i.e., a superelastic material such as nitinol, which is held by the catheter 24 in a compressed state during insertion into the heart 32. When the distal segment 28 of the catheter 24 reaches the operative site at which the stent 20 is to be deployed, such as within the pulmonary vein 22, the catheter 24 releases the stent 20. The elastic properties of the stent material cause the stent 20 to expand outward, thus anchoring the stent 20 against the inner wall of the pulmonary vein 22.

Referring again to FIG. 1, typically the stent 20 is positioned within or at the ostium of a pulmonary vein or within a pulmonary vein near the ostium. In some applications it may be required that instances of the stent 20 be placed in multiple pulmonary veins, or even in all of the pulmonary veins. Placement of an intravascular catheter and delivery of a stent on an anchoring balloon is described in commonly assigned application Ser. No. 10/062,698, entitled "Radio Frequency Pulmonary Vein Isolation", which is herein incorporated by reference. As the techniques of cardiac catheterization are well-known in the art, further description is omitted in the interest of brevity.

After the stent 20 is inserted, the catheter 24 is usually withdrawn from the proximity of the target tissue 12, leaving the stent 20 in place. Generally, the catheter 24 remains in the left atrium in order to monitor the ablation process, using the monitoring electrode 30. The control unit 18 then drives the transmitters 16 to generate an electromagnetic field at the resonant frequency $f_r$ of the stent 20. A power output from the transmitters 16 of 50 watts at a frequency of 13.56 MHz is suitable. The stent 20 experiences this electromagnetic field, and re-radiates electromagnetic energy at the resonant frequency $f_r$. The target tissue 12 absorbs re-radiated RF energy, raising the temperature of the target tissue 12 to about 50 degrees C., which ablates the target tissue 12, and produces non-electroconductive lesions, thereby creating a conduction block. Alternatively or additionally, the temperature of the stent 20 itself increases responsive to the electromagnetic fields of the transmitters 16, which accomplishes ablation by direct conduction of heat from the stent 20 to the target tissue 12.

Typically, the lesions produced by the ablation form one or more circumferential conduction blocks around a pulmonary vein at or near the sites of contact of the stent with the pulmonary vein. In one application, if an arrhythmia originates from an identified location in a pulmonary vein, a circumferential conduction block is formed along a path of the wall tissue that either includes the arrhythmogenic origin, thereby eliminating the source, or the block is formed between the origin and the left atrium, thereby preventing conduction of unwanted signals.

Figure 3:
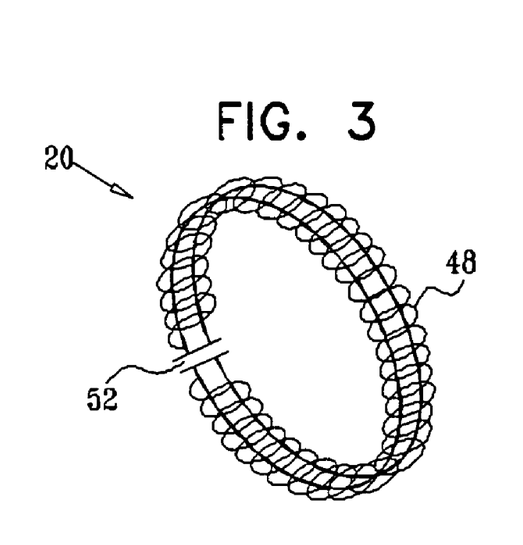
FIG. 3 is an enlarged schematic diagram of a stent having a resonant response to an electromagnetic field for use in the system of FIG. 1 in accordance with a disclosed embodiment of the invention.

Reference is now made to FIG. 3, which is an enlarged schematic diagram illustrating electrical aspects of the stent 20 (FIG. 1), which is constructed and operative in accordance with a disclosed embodiment of the invention. The stent 20 comprises the coil 48 and a capacitor 52, which is electrically connected to the coil 48. As seen in FIG. 3 the capacitor is formed as a core constituted as a split ring and the coil 48 is wound on the capacitor, the overall shape of the stent 20 is a ring. The coil 48 is made of a resistive metal such as nitinol having elasticity and a shape memory. The coil 48 typically has approximately 15 loops. Because of its geometry the coil 48 behaves as an inductor. It should be noted that in choosing the reactance of the coil 48, a tradeoff is required between the desirability of a high quality factor (Q) to assure efficient power transfer, and the resistive heat desired to be developed in the stent circuit. This tradeoff will be readily apparent to those skilled in the art from a consideration of the basic physics governing the operation of such circuits.

Preferably, the stent 20 is calibrated at the time of manufacture to determine its precise resonant frequency, which may vary based on manufacturing variations of both the inductor, the capacitor, and the precise geometry of the stent. However, it may be desirable to determine the precise resonant frequency when the stent 20 is in is operative position. This can be accomplished inductively, using a dip meter.

In some embodiments, the stent 20, including the coil 48, is made of a biodegradable material, for example polymer polylactide and trimethylene carbonate polymers. After insertion, the stent 20 remains firmly engaged circumferentially with the inner lining of the pulmonary vein as a result of its elasticity and shape memory. In these embodiments, the stent 20 is allowed to remain in situ following the ablation procedure, and it is eventually resorbed. While it remains intact, the stent 20 may continue to function as a re-radiator of RF energy from the transmitters 16, should repeated ablative procedures be required. In such embodiments, the continued presence of the stent 20 in the pulmonary vein may have the additional benefit of reducing the risk of contracture and stenosis of the pulmonary veins. In still other embodiments, besides remaining in situ, the stent 20 is also coated with a drug, which acts locally to prevent stenosis of the vessel or delivers other desired therapy, as disclosed in the above-noted application Ser. No. 10/062, 698.

Although the capacitor 52 is shown in FIG. 3 as a discrete component, the inherent capacitance of the material of the stent itself is also significant in determining the resonant frequency of the stent 20. In some embodiments, this inherent capacitance is sufficient to give the desired resonance, in which case a separate capacitor is not needed.

Figure 5:
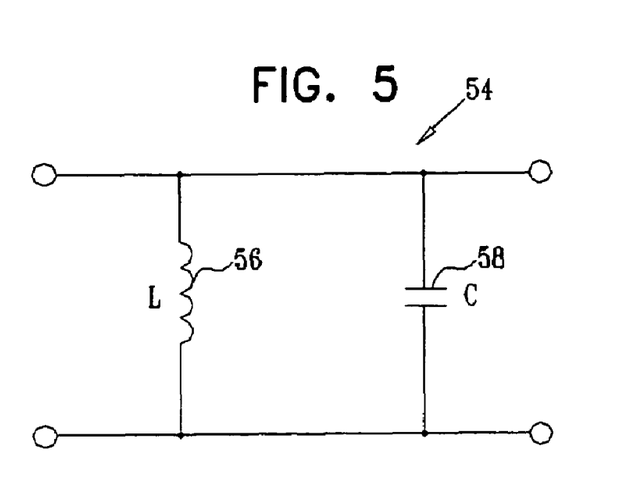
FIG. 5 is an electrical schematic of an equivalent circuit for the stent shown in FIG. 3.

Reference is now made to FIG. 5, which is an electrical schematic of a parallel LC resonant circuit 54. The circuit 54 is an equivalent circuit for the stent 20 (FIG. 3). The circuit 54 comprises an inductor 56 and a capacitor 58 connected thereacross, the values being chosen so that the resonant frequency $f_r$ of the circuit 54 corresponds to the frequency of the RF electromagnetic field to be applied by the transmitters 16. In embodiments of the present invention with a single capacitor, as shown in FIG. 3 and FIG. 5, the resonant frequency $f_r$ is given by:

$$f_r = \frac{1}{2\pi\sqrt{LC}}$$

where L is the inductance of the inductor 56, and C is the capacitance of the capacitor 58.

A resonant frequency that does not correspond to any clinically relevant frequencies or harmonics thereof should be used, such as 13.56 MHz. If, for example, the capacitor 58 has a capacitance C of 60 pF, and the inductor 56 has an inductance L of 2.30 µH, a resonant frequency $f_r$ of 13.56 MHz results. The inductor 56 is designed and manufactured so as to be characterized by a quality factor of at least 100 at 13.56 MHz.

Figure 4:
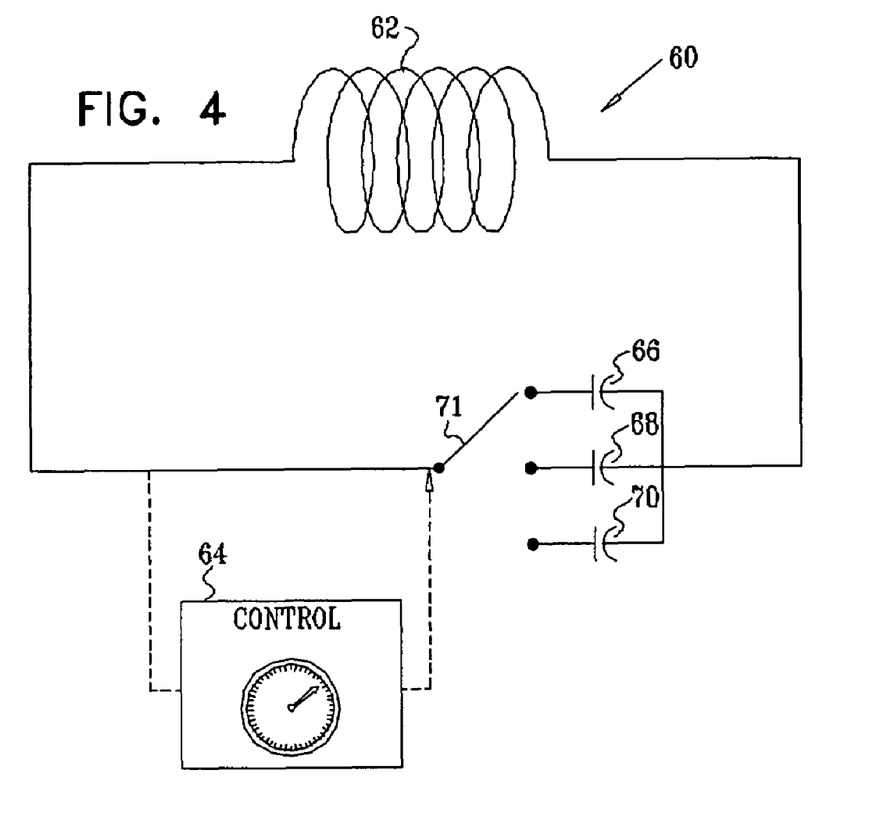
FIG. 4 schematically illustrates a stent circuit having an automatic calibration circuit, which is constructed and operative in accordance with an alternate embodiment of the invention.

Reference is now made to FIG. 4, which schematically illustrates a stent circuit 60, which is constructed and operative in accordance with an alternate embodiment of the invention. The resonant frequency of the stent circuit 60 can be selected to match the output of a transmitter. The stent circuit 60 may be used as the stent 20 in the system 10 (FIG. 1). The stent circuit 60 comprises a coil 62 comprising one or more loops of wire made of a resistive alloy, such as Nitinol or a nickel-chromium alloy. A control chip 64 is included in the stent circuit 60, and is responsive to current flowing therethrough. The control chip 64 automatically operates the switch 71 to switch capacitors 66, 68, 70 into the circuit sequentially, and locks the capacitor into the circuit that results in a resonant frequency that most closely approximates that of the transmitter. This embodiment has the advantage of adaptively changing the resonant frequency of the stent, which is useful if the size and/or shape of the stent is to be adjusted during implantation in the pulmonary vein, for example by expanding the stent using a balloon. Such changes in size also change the inductance of the coil, and therefore affect the resonant frequency of the circuit, which may then be adjusted by selecting the proper capacitor. The possibility of adjusting the resonant frequency by capacitor selection is also useful if more than one stent needs to be implanted and selectively energized in the same patient. The transmitter can then be tuned to the frequency of the stent needing activation.

Operation

Figure 6:
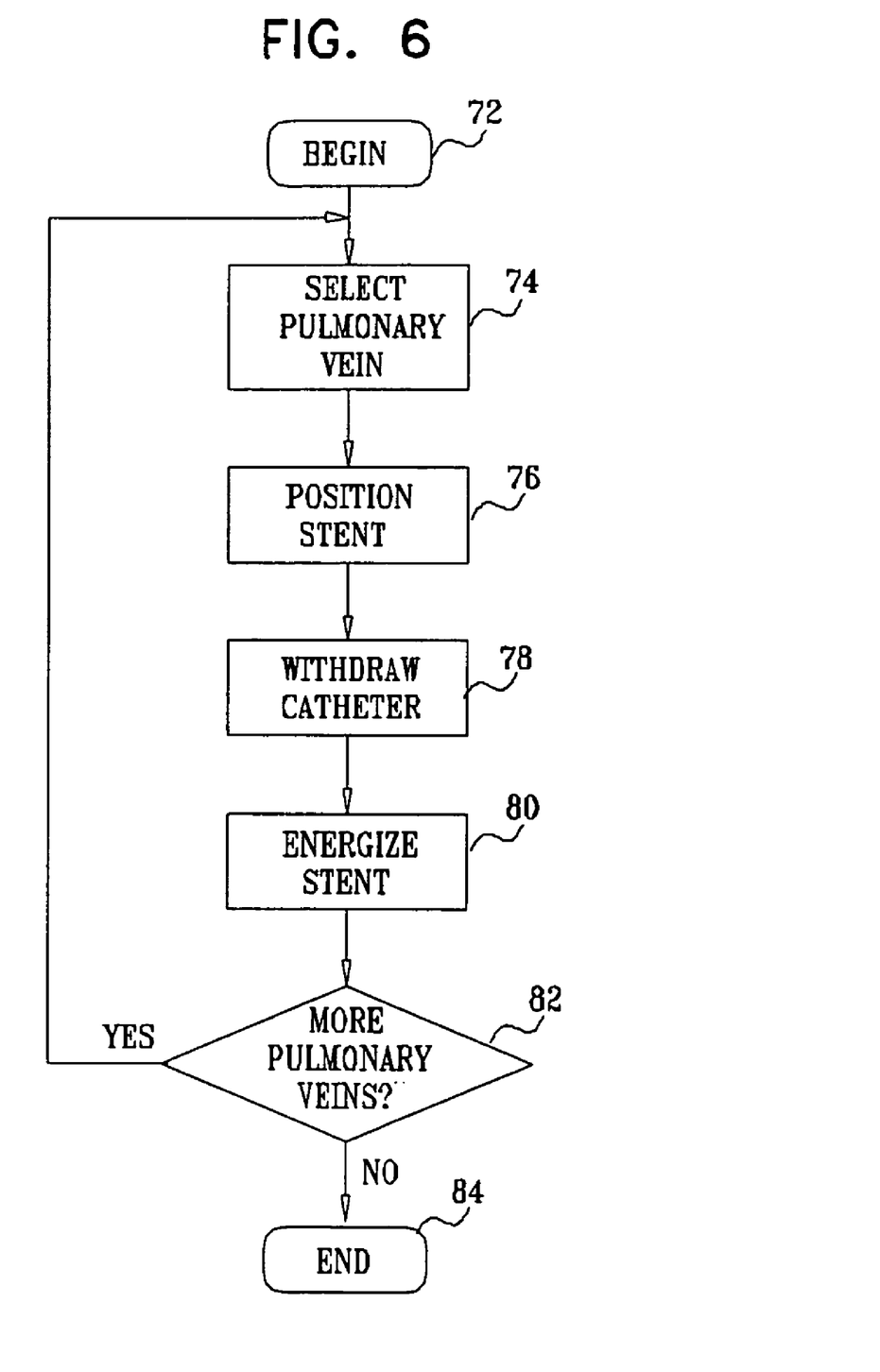
FIG. 6 is a flow chart illustrating a method of electrical isolation of a pulmonary vein in accordance with a disclosed embodiment of the invention.

Reference is now made to FIG. 6, which is a flow chart illustrating a method of electrical isolation of a pulmonary vein in accordance with a disclosed embodiment of the invention. The procedure begins at initial step 72, in which catheterization of the heart is accomplished. A resonant stent is removably affixed to an intravascular catheter. The venous system may be accessed using the well-known Seldinger technique, in which an introducer sheath is positioned in a peripheral vein, typically a femoral vein. A guiding sheath is introduced through the introducer sheath, and is advanced via the inferior vena cava into the right atrium. Then, using a Brockenbrough needle, the fossa ovalis of the interatrial septum is punctured, and the puncture dilated if necessary. The Brockenbrough needle is withdrawn, and the guiding sheath placed in the left atrium. Alternatively, other methods known in the art may be used to access the left atrium, with or without the assistance of a guiding sheath and guidewire, as described below.

Next, at step 74, a pulmonary vein is chosen, and a guidewire is advanced through the guiding sheath, through the left atrial chamber, and into the selected pulmonary vein. The order in which the specific pulmonary veins are visited and treated is arbitrary, but it is preferable to concentrate first on the two superior pulmonary veins, in which the muscular sleeves are more prominent than in the inferior pulmonary veins. Thereafter, the inferior pulmonary veins may be isolated. Typically, an ablation procedure involves the isolation of all four pulmonary veins.

Next, at step 76, the guiding sheath is withdrawn, and an ablation catheter is slidably tracked over the guidewire, using the guidewire lumen of the catheter. The catheter is advanced into the left atrium. While maneuvering the catheter in the heart, its position may be monitored by a location and mapping system as disclosed in the above-noted U.S. Pat. No. 5,840,025, or alternatively by conventional imaging modalities. During placement, the anchoring balloon of the catheter remains deflated, and the stent is radially collapsed about the exterior wall of the anchoring balloon. The diameter of the collapsed stent is smaller than the diameter of the pulmonary vein, such that the stent is movable within the lumen of the vein. The stent is positioned at or within the ostium of the selected pulmonary vein. The stent is caused to expand radially, and to engage a circumferential area of the inner lining of the pulmonary vein in which the target tissue is located.

Expansion of the stent is accomplished by inflating the balloon, which urges the stent radially outward toward the inner wall of the pulmonary vein. In some embodiments, the shape memory of the coil alloy can be exploited to cause the stent to expand by resistively heating the coil, or the coil may be sufficiently elastic to expand of its own accord when released by the catheter. The radially expanded stent engages the pulmonary vein in a continuous line that runs circumferentially about the pulmonary vein proximate its ostium, such that the principal axis of the stent is substantially aligned coaxially with the pulmonary vein. Perfusion of the area through a catheter port may be employed in order to minimize stasis of blood in the region, particularly in embodiments in which resistive heating of the stent is a predominant effect. Optionally, where stenting is not intended, the coil is not expanded.

Next, at step 78, once the position of the coil is confirmed, the catheter is withdrawn. In embodiments in which the stent is carried on a balloon, the balloon is deflated. The catheter is repositioned within the left atrium, so that signals from its monitoring electrodes can inform the operator as to the progress of the ablation. When stenting is not required, the catheter is not withdrawn.

Next, at step 80, the external radiofrequency transmitter is energized, and radiofrequency energy is conducted from the transmitter to the stent. The stent, being resonant at the frequency of the transmitter, re-radiates radiofrequency energy. The transfer of radiofrequency energy from the stent to the pulmonary vein occurs in a single, relatively short application. An external radiofrequency generator is configured such that reradiated RF energy should heat the target tissue to about 50 degrees C. The energy application may be controlled in response to continuous electrophysiological monitoring, an end point being reached when a conduction block is confirmed across the line of ablation. Alternatively, the end point could be delivery of a predetermined amount of energy to the target tissue, or the expiration of a time interval. The stent is generally left in place following the procedure. Optionally, it can be removed.

Control now proceeds to decision step 82, where a determination is made whether more pulmonary vein ostia remain to be treated. If the determination at decision step 82 is affirmative, then control returns to step 74. In subsequent iterations of steps 74-80, it is desirable that each of the stents emplaced in different pulmonary veins have different resonant frequencies, in order to individualize the transfer of energy to each pulmonary vein without affecting other pulmonary veins. Alternatively, if only one resonant frequency is employed for multiple stents, then step 80 should be deferred until completion of stenting of all the pulmonary veins in order to prevent reheating of previously ablated areas.

If the determination at decision step 82 is negative, the process ends at final step 84.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A system for electrically isolating a cardiac chamber, comprising:
    a resonant circuit having a resonant frequency, said resonant circuit being constructed and dimensioned for introduction into an operative position in a pulmonary vein of a subject proximate an ostium of said pulmonary vein;
    a catheter adapted to carry said resonant circuit into said operative position in said pulmonary vein;
    a stent dimensioned for circumferential engagement with an inner wall of said pulmonary vein to define a circumferential region of contact between said stent and said pulmonary vein, wherein a principal axis of said stent is substantially aligned coaxially with said pulmonary vein, said resonant circuit being incorporated in said stent; said stent and said resonant circuit forming a body in the shape of a ring, wherein said ring comprises a capacitor core and an inductor coil wound around said capacitor core;
    a generator disposed external to said subject for generating an electromagnetic field that has a frequency substantially equal to said resonant frequency of said resonant circuit, said electromagnetic field operatively including said resonant circuit and causing said resonant circuit to re-radiate electromagnetic energy so as to ablate intramural target tissue in said pulmonary vein; and
    a sensor system to position and orient said stent in said pulmonary vein proximate the ostium of the pulmonary vein so that when the target tissue of the pulmonary vein has been ablated, a coronary chamber communicating with the pulmonary vein at said ostium will be electrically isolated from the pulmonary vein.

2. The system according to claim 1, further comprising a sensor for monitoring electrophysiologic cardiac properties of said subject for determining if a predefined end point has been reached.

3. The system according to claim 2, wherein said predefined end point comprises confirmation of a block of electrical conductivity at said target tissue.

4. The system according to claim 1, further comprising:
    a plurality of capacitors in said resonant circuit; and
    a control circuit for automatically selecting one of said capacitors responsively to a frequency of said electromagnetic field so as to conform said resonant frequency of said resonant circuit with said frequency of said electromagnetic field.

5. The system according to claim 1, wherein said stent is constructed of an alloy having a shape memory.

6. The system according to claim 1, wherein said stent is constructed of a biodegradable material.

7. The system according to claim 1, further comprising: a localizing subsystem for tracking a position and orientation of said catheter, comprising:
    a plurality of localizing field generators disposed external to said subject;
    a position sensor on said catheter that is responsive to localizing electromagnetic fields produced by said localizing field generators; and
    a receiver responsive to an output of said position sensor.

8. The system according to claim 1 wherein said ring is oriented in a plane extending radially of the axis of the pulmonary vein.

9. The system according to claim 8 wherein said stent is positioned in facing relative to the ostium of the pulmonary vein.

10. The system according to claim 9 wherein the position of the stent relative to said ostium is such that the target tissue is ablated near said ostium to block electrical conductivity of said tissue and thereby counteract arrhythmia in the heart chamber.

11. The system according to claim 1, wherein the stent and the resonant circuit form the body in the shape of a ring such that a surface of the body has a width that is smaller than the diameter of the body.

12. In a system for electrically isolating a cardiac chamber, the improvement comprising:
- a stent for circumferential engagement with an inner wall of a pulmonary vein of a subject proximate an ostium of said pulmonary vein to define a circumferential region of contact between said stent and said pulmonary vein, a principal axis of said stent being oriented substantially coaxial with said pulmonary vein;
- a resonant circuit having a resonant frequency incorporated in said stent, said stent and said resonant circuit forming a ring-shaped body comprising a capacitor core and an inductor coil wound around said capacitor core;
- a generator for disposal external to said subject and generating an electromagnetic field that has a frequency substantially equal to said resonant frequency; said electromagnetic field operatively including said resonant circuit, whereby said resonant circuit re-radiates electromagnetic energy so as to ablate intramural target tissue in said pulmonary vein; and
- a sensor system for engaging and orienting said stent in said pulmonary vein proximate said ostium of said pulmonary vein whereby, when the target tissue in said pulmonary vein has been ablated, a coronary chamber communicating with the pulmonary vein at said ostium will be electrically isolated from the pulmonary vein.

13. A method for electrically isolating a cardiac chamber of a patient, comprising the steps of:
- a) providing the system of claim 12;
- b) engaging and orienting the stent in the pulmonary vein of the patient proximate the ostium of the pulmonary vein; and
- c) ablating the target tissue in the pulmonary vein with electromagnetic energy re-radiated from said resonant circuit to electrically isolate the coronary chamber from the pulmonary vein.

* * * * *